US009752956B2

(12) United States Patent
McKimpson et al.

(10) Patent No.: US 9,752,956 B2
(45) Date of Patent: Sep. 5, 2017

(54) MONITORING SYSTEM FOR PREDICTING GEARBOX LIFESPAN

(71) Applicant: Caterpillar Inc., Peoria, IL (US)

(72) Inventors: Marvin Grendel McKimpson, Germantown Hills, IL (US); Richard Andrew Carpenter, Chillicothe, IL (US)

(73) Assignee: Caterpillar Inc., Peoria, IL (US)

( * ) Notice: Subject to any disclaimer, the term of this patent is extended or adjusted under 35 U.S.C. 154(b) by 178 days.

(21) Appl. No.: 14/642,652

(22) Filed: Mar. 9, 2015

(65) Prior Publication Data

US 2016/0266006 A1 Sep. 15, 2016

(51) Int. Cl.
*G01M 13/02* (2006.01)
*G01N 33/28* (2006.01)
*G01N 15/06* (2006.01)
*G01N 3/56* (2006.01)
*G01N 15/02* (2006.01)
*G01N 15/00* (2006.01)

(52) U.S. Cl.
CPC ...... *G01M 13/021* (2013.01); *G01N 33/2888* (2013.01); *G01N 3/56* (2013.01); *G01N 15/02* (2013.01); *G01N 15/06* (2013.01); *G01N 33/2858* (2013.01); *G01N 2015/0053* (2013.01)

(58) Field of Classification Search
CPC ....... G01M 13/021; G01N 3/56; G01N 15/02; G01N 15/06; G01N 33/2888
See application file for complete search history.

(56) References Cited

U.S. PATENT DOCUMENTS

| 5,777,211 A | 7/1998 | Binienda et al. |
| 6,839,620 B1 | 1/2005 | Koehler et al. |
| 7,914,250 B2 | 3/2011 | Behera et al. |
| 8,050,814 B2 | 11/2011 | Rains et al. |
| 8,645,018 B2 | 2/2014 | Lee |
| 2014/0088888 A1* | 3/2014 | Poon ...................... F03B 15/00 702/34 |
| 2015/0168199 A1* | 6/2015 | Eck ........................ G01F 1/704 702/45 |

* cited by examiner

*Primary Examiner* — Hezron E Williams
*Assistant Examiner* — David Z Huang
(74) *Attorney, Agent, or Firm* — Finnegan, Henderson, Farabow, Garrett & Dunner, LLP

(57) ABSTRACT

A monitoring system for a gearbox containing a lubricant is disclosed. The monitoring system may include a first sensor configured to measure a concentration of debris particles in the lubricant, a second sensor configured to generate data indicative of a deterioration of the gearbox, and a controller in communication with the first and second sensors. The controller may be configured to estimate a concentration of debris particles in the lubricant based on the data from the second sensor using a mathematical function, and estimate a remaining useful life of the gearbox based on a difference between concentration of debris particles measured by the first sensor and concentration of debris particles estimated to be in the lubricant.

18 Claims, 2 Drawing Sheets

MONITORING SYSTEM FOR PREDICTING GEARBOX LIFESPAN

TECHNICAL FIELD

The present disclosure relates generally to a monitoring system and, more particularly, to a monitoring system for predicting the lifespan of a gearbox.

BACKGROUND

Many mobile and stationary machines employ drive systems that transmit mechanical energy from an input end to an output end for performing various tasks. Where control of certain drive system output parameters (e.g., speed, torque, direction of rotation or travel, etc.) is desired, mechanical devices, such as gearboxes, are commonly connected between the input end and the output end of the drive system. A gearbox typically includes a number of components that work together to transmit power, such as gears, shafts, and bearings that are protected from their surroundings in a sealed container. A gearbox typically requires constant lubrication to reduce friction and keep the internal components cool during operation. As the components wear and/or fail over the useful life of a gearbox, they can shed debris particles that accumulate in the lubricant and necessitate periodic repairs and/or lubricant replacement.

Repairing or replacing a gearbox requires that the associated machine be temporarily taken out of service, which can decrease productivity. One way to reduce loss of productivity is to predict when a gearbox is going to fail and to perform periodic maintenance prior to failure. To predict gearbox failures and facilitate planning of future gearbox maintenance, manufacturers have implemented gearbox monitoring systems. Some gearbox monitoring systems predict the lifespan of gearboxes using mathematical functions. In particular, the mathematical functions predict future wearing of components based on historic data and current gearbox operating parameters. However, variations in operating conditions, component flaws, load variances, unexpected failures, and other inconsistencies may cause known gearbox monitoring systems to produce inaccurate estimations of gearbox lifespan.

One attempt to estimate the lifespan of a gearbox is described in U.S. Pat. No. 7,914,250 (the '250 patent) that issued to Behera et al. on Mar. 29, 2011. The '250 patent describes a gearbox lifespan estimation system that includes a number of sensors associated with various shafts, gears, and bearings within a gearbox. The sensors generate field data, such as a number of start-ups, load sequences, oil quality, vibrations, component speeds, and the power output of the gearbox. The field data is used in a model to simulate the total power input to the gearbox and the individual loads experienced by each gearbox component due to the load input. The field data is also used in an algorithm for determining physical faults associated with the gearbox components, such as cracked or broken gear teeth and bearing damage. The faults are used to estimate additional loads experienced by the individual gearbox components caused by the faults. A total load on each component is then estimated by summing the load caused by the input power to the gearbox and the load caused by the faults. The lifespan of the gearbox is estimated to be the shortest lifespan of the individual components based on the total estimated loads.

Although the system of the '250 patent may be somewhat effective at determining the lifespan of a gearbox, it may not be optimum. In particular, the system of the '250 patent may determine the gearbox lifespan based only on estimated loads of the gearbox, which may render the lifespan estimation inaccurate when the estimated loads are themselves inaccurate. Further, the system of the '250 patent may not be able to determine when the models and algorithms used to estimate the gearbox lifespan are inaccurate or correct their inaccuracies.

The gearbox monitoring system of the present disclosure solves one or more of the problems set forth above and/or other problems of the prior art.

SUMMARY

In one aspect, the present disclosure is directed to a monitoring system for a gearbox containing a lubricant. The monitoring system may include a first sensor configured to measure a concentration of debris particles in the lubricant, a second sensor configured to generate data indicative of a deterioration of the gearbox, and a controller in communication with the first and second sensors. The controller may be configured to estimate a concentration of debris particles in the lubricant based on the data from the second sensor using a mathematical function, and estimate a remaining useful life of the gearbox based on a difference between the concentration of debris particles measured by the first sensor and the concentration of debris particles estimated to be in the lubricant.

In another aspect, the present disclosure is directed to a method of monitoring a gearbox. The method may include measuring a concentration of debris particles in a lubricant of the gearbox, determining data indicative of a deterioration of the gearbox, and estimating a concentration of debris particles in the lubricant based on the data using a mathematical function. The method may further include estimating a remaining useful life of the gearbox based on a difference between the concentration of debris particles measured and the concentration of debris particles estimated to be in the lubricant.

In yet another aspect, the present disclosure is directed to a mobile machine. The machine may include a frame, a power source mounted to the frame, a traction device mounted to the frame, and a gearbox drivingly connected between the power source and the traction device, the gearbox containing a lubricant. The machine may further include a first sensor configured to measure a concentration of debris particles in the lubricant, a second sensor configured to generate data indicative of a deterioration of the gearbox, and a controller in communication with the first and second sensors. The controller may be configured to estimate a concentration of debris particles in the lubricant based on the data from the second sensor using a mathematical function, and estimate a remaining useful life of the gearbox using the mathematical function when a difference between the concentration of the debris particles measured by the first sensor and the concentration of debris particles estimated to be in the lubricant over a period of time is below a first threshold difference. The controller may be further configured to correct the mathematical function when the difference between the concentration of debris particles measured by the first sensor and the concentration of debris particles estimated to be in the lubricant over the period of time is above the first threshold difference and below a second threshold difference.

DETAILED DESCRIPTION

Figure 1:
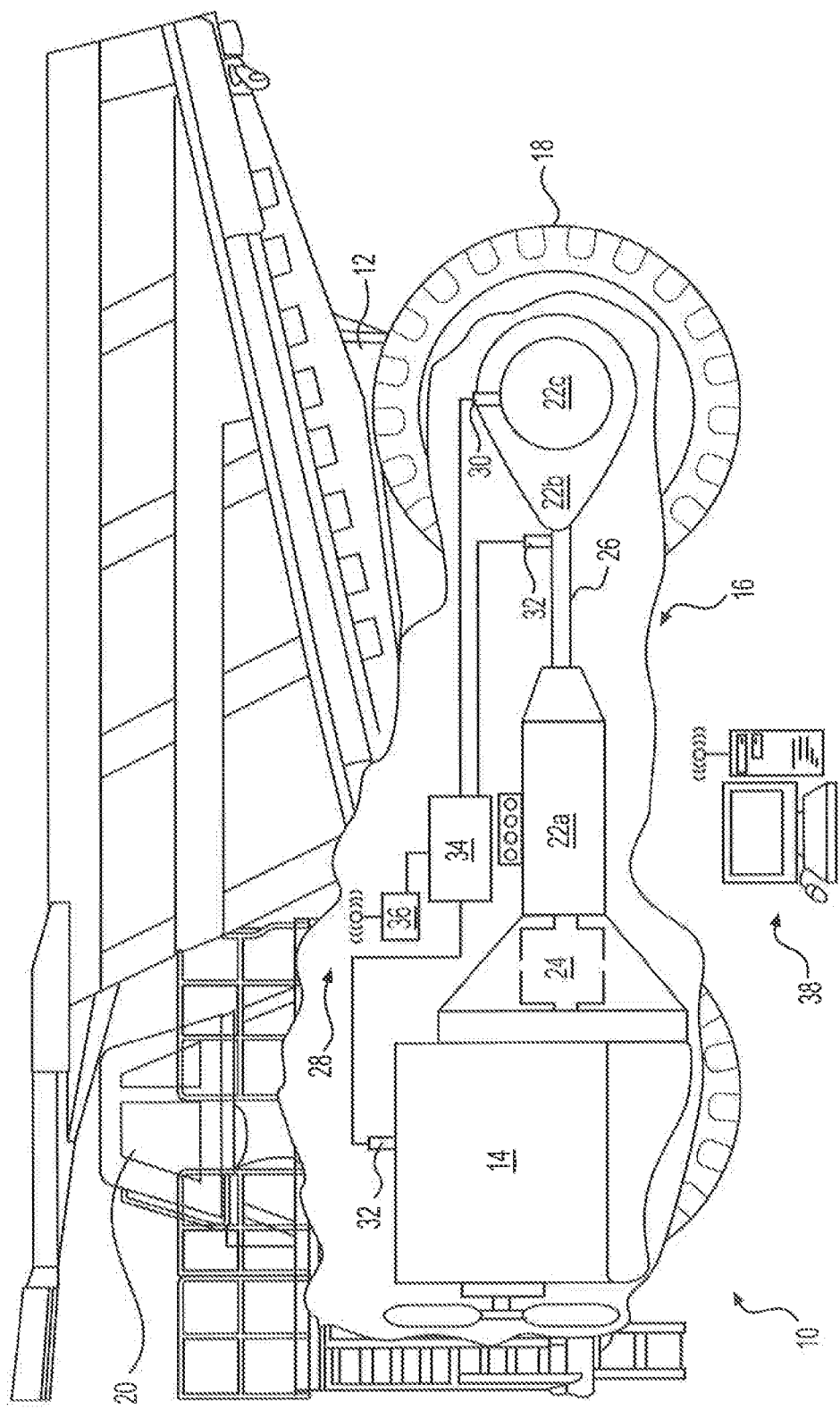
FIG. 1 is a diagrammatic illustration of a machine incorporating an exemplary disclosed gearbox monitoring system.

FIG. 1 illustrates an exemplary mobile machine 10. Machine 10 may perform some type of operation associated with an industry such as mining, construction, farming, transportation, or any other industry. For example, machine 10 may be an earth moving machine such as an off-highway haul truck, a wheel loader, a motor grader, or any other suitable earth moving machine. Machine 10 may alternatively embody an on-highway vocational truck, a passenger vehicle, or any other operation-performing machine. Although machine 10 is embodied in FIG. 1 as an off-highway haul truck, it understood that machine 10 may embody a stationary type of machines such as a drilling system, a pumping system, a wind turbine, a wave energy converter, or any other machine having a mechanical energy input and/or output. Machine 10 may include, among other things, a frame 12, a power source 14 mounted to frame 12, a drive system 16 driven by power source 14, one or more traction device(s) 18 connected to frame 12 and driven by drive system 16, and an operator station 20 mounted to frame 12 for controlling operations of machine 10.

Power source 14 may be configured to produce a power output and may be an internal combustion engine. For example, power source 14 may be a diesel engine, a gasoline engine, a gaseous fuel-powered engine, or any other type of engine. It is understood that power source 14 may alternatively be a non-combustion power source such as, for example, a battery, a fuel cell, a motor, or any other type of non-combustion source of power.

Drive system 16 may be configured to transfer the power output from power source 14 to traction devices 18. One or more of gearboxes 22a-c may form a portion of drive system 16 and be configured to receive the output of power source 14 and collectively drive traction devices 18 with desired output characteristics. For example, gearboxes 22a-c may include a transmission 22a, a differential 22b, and one or more final drive unit(s) 22c (only one shown in FIG. 1). Although they are shown as separate units in FIG. 1, gearboxes 22a-c may alternatively be combined in a single axle assembly. Drive system 16 may include fewer or different types of gearboxes than gearboxes 22a-c as mentioned above. For example, in other embodiments, drive system 16 may further or alternatively include a front axle assembly having one or more final drive units connected via a front differential and/or a transfer case to transmission 22a or power source 14 for driving one or more front-end traction devices. It is understood that other configurations of drive system 16 may be possible.

Transmission 22a may include numerous components that interact to transmit power from power source 14 to traction device(s) 18. For example, transmission 22a may embody a multi-speed, bidirectional, mechanical transmission having a plurality of gears (not shown) that are selectable to change the output speed and torque of transmission 22a. The gears and other components (e.g., bearings, seals, valves, etc.) of transmission 22a may be lubricated and cooled by a lubricant system (not shown) connected to transmission 22a. The lubricant system may include a sump for holding a lubricant (e.g., a lubricant oil or other fluid) a pump, a filter, and a cooling device (e.g., a heat exchanger). Over time, debris particles and other contaminants may accumulate in the lubricant of transmission 22a. The debris particles may include wear particles generated within transmission 22a (i.e. particles shed by the gears and bearings caused by wear and/or failure) and external contaminants (e.g., dirt, sand, dust, fluid from other fluid circuits etc.). Accumulation of debris particles over time and/or failure of bearings and seals may necessitate periodic replacement of the lubricant and/or transmission 22a.

Transmission 22a may be a single-clutch automatic transmission, and may be coupled to power source 14 via a torque converter 24. In other embodiments, transmission 22a may embody another type of automatic transmission, such as a multi-clutch automatic transmission. Transmission 22a may alternatively embody a manual-shift transmission and include a number of gears connectable to power source 14 via a manually operated clutch and gear selector. It is understood that transmission 22a may embody any suitable type of transmission for transferring mechanical energy between power source 14 and traction device(s) 18.

Differential 22b may include a number of parts (e.g., gears, bearings, shafts, etc.) that interact to transmit power from transmission 22a to other components of drive system 16. For example, differential 22b may be configured to receive power from transmission 22a via a shaft 26 that rotates at a speed and with an amount of torque determined by settings of transmission 22a. Differential 22b may be further configured to create rotation around an axis that is not parallel with shaft 26 (e.g., perpendicular to shaft 26).

Differential 22b may also contain a lubricant for cooling and reducing wear of the gears and bearings therein. The lubricant may be delivered to differential 22b via an external lubricant system, which may include a sump, a pump, a filter, a cooling device, etc. Alternatively, the lubricant within differential 22b may be contained solely within differential 22b. Over time, wear particles and external debris particles (e.g., dirt, other fluids, etc.), may contaminate the lubricant and necessitate periodic replacement of the lubricant or components of differential 22b.

Final drive 22c may include a number of parts (e.g., gears, bearings, shafts, etc.) that interact to transmit power from differential 22b to traction device(s) 18. Final drive 22c may include a set of gears (e.g., planetary gears or other types of gears) having a gear ratio configured to reduce the speed and increase the torque output of traction device(s) 18. A separate final drive 22c may be assigned to each traction device 18.

Final drive 22c may also contain a lubricant for cooling and reducing wear of the gears and bearings therein. The lubricant may be delivered to final drive 22c via a dedicated lubricant system, which may include a sump, a pump, a filter, a cooling device, etc. Alternatively, final drive 22c may share the lubricant system of differential 22b. In some embodiments, the lubricant for final drive 22c may be contained solely within final drive 22c. Over time, debris particles, such as wear particles (e.g., particles shed from gears, bearings, etc.) and external debris particles (e.g., dirt, other fluids, etc.), may contaminate the lubricant and necessitate periodic replacement of the lubricant or components of final drive 22c.

Drive system 16 may further include a gearbox monitoring system 28 configured to estimate the remaining useful life of one or more of gearboxes 22a-c. As components (e.g., gears, bearings, etc.) within gearboxes 22a-c wear and/or fail and shed debris particles, the concentration of debris particles in the lubricant may be indicative of a remaining useful life of the gearbox or its lubricant. In some embodiments, the remaining useful life of gearboxes 22a-c may be the time remaining until one of the components of a respective gearbox 22a-c fails or has worn beyond a tolerable level. In other embodiments, the remaining useful life of gearboxes 22a-c may be the amount of time remaining until the lubricant becomes contaminated beyond a tolerable limit. In other embodiments, the remaining useful life of gearboxes 22a-c may be a probability that gearboxes 22a-c will reach a next service interval without requiring service (e.g., replacement, repair, lubricant change, etc.) sooner. A service interval may be an amount of time (e.g., a number of hours, etc.) or a distance traveled (e.g., a number of miles, etc.) after which maintenance (e.g., inspection, repair, replacement, lubricant change, etc.) is regularly performed on gearboxes 22a-c.

Gearbox monitoring system 28 may include a particle sensor 30 for measuring the concentration and size of debris particles in the lubricant of gearboxes 22a-c. Gearbox monitoring system may also include one or more sensors 32 configured to generate data indicative of a load on one or more of gearboxes 22a-c. Sensors 30 and 32 may be in communication with a controller 34 configured to receive and process gearbox data and estimate the remaining useful life of one or more of gearboxes 22a-c and their lubricants. Controller 34 may be electronically connected to a communication module 36 configured to transmit data to an off-board computer 38. In the example of FIG. 1, particle sensor 30 is associated with final drive 22c. It is contemplated, however, that particle sensor 30 may be associated with any of gearboxes 22a-c or with any other gearbox not shown in FIG. 1. It is also contemplated that each of gearboxes 22a-c may be equipped with its own particle sensor 30.

Particle sensor 30 may be an optical sensor configured to use a light source to illuminate and count individual particles passing through a detection chamber. Particle sensor 30 may be further configured to determine a size of each counted particle and tabulate counted particles according to their size or size distribution among a range of sizes. For example, particle sensor 30 may be configured to count debris particles ranging from 1 to 100 µm. It is understood, however, that particle sensor 30 may be configured to count debris smaller than 1 µm and/or greater than 100 µm, if desired. Particle sensor 30 may report particle data in any suitable format, such as a number of particles of a certain size per milliliter of lubricant. Alternatively, concentrations of debris particles may be reported as numbers of a code system provided by the International Organization for Standardization (ISO). ISO code numbers may indicate a particular distribution or range of concentrations in which the measured concentration is included for a given size of debris particle. In other embodiments, particle sensor 30 may be an electromagnetic sensor or other type of sensor for determining a concentration of debris particles in the lubricant.

Sensors 32 may be configured to measure, calculate, or otherwise determine data indicative of deterioration of one or more of gearboxes 22a-c. That is, sensors 32 may embody physical and/or virtual sensors configured to determine parameters of power source 14 and drive system 16 that may be used by controller 34 to determine a service profile that represents the deterioration of gearboxes 22a-c over time. For example, sensors 32 may be configured to determine one or more of a speed of power source 14, an output torque of power source 14, a throttle position of power source 14, output and/or input torques of gearboxes 22a-c, output and/or input speeds of gearboxes 22a-c, a speed of traction device(s) 18, a temperature (e.g., ambient, of power source 14, of gearboxes 22a-c, etc.), and one or more lubricant parameters (e.g., temperature, viscosity, pressure, etc.). Sensors 32 may also be configured to determine a payload and/or axle load of machine 10, which may be indicative of deterioration of internal components of gearboxes 22a-c, such as bearings. Sensors 32 may be configured to communicate data to controller 34 for further processing.

Controller 34 may embody a one or more microprocessors, computers, and/or modules configured to estimate the remaining useful life of gearboxes 22a-c. The microprocessors, computers, and/or modules of controller 34 may be contained within a single enclosure or located some distance from each other. Numerous commercially available microprocessors, computers, and/or modules can be configured to perform the functions of controller 34. It should be appreciated that controller 34 could readily embody a general machine controller capable of controlling numerous machine functions. Controller 34 may also include a memory (e.g., RAM, ROM, flash disk, hard drive, CD, DVD, magnetic disk or tape, etc.) for storing particle concentration data, models, algorithms, maps, and other types of data and instructions. Various other circuits may be associated with controller 34, including power supply circuitry, signal-conditioning circuitry, solenoid driver circuitry, communication circuitry, and other appropriate circuitry.

Communication module 36 may include any device that facilitates communication of data between machine 10 and off-board computer 38. Communication module 36 may include hardware and/or software that enables sending and/or receiving data through a wireless communication link, a direct data link, or by a voice commination device, such as a two-way radio. In some cases, communication module 36 may include a portable data recording medium, and data may be transferred from machine 10 to off-board computer 38 using the portable data recording medium.

Off-board computer 38 may embody an electronic device configured to process and/or display data (e.g., data indicative of the deterioration of gearboxes 22a-c, the remaining useful life of gearboxes 22a-c, etc.) to personnel. For example, off-board computer 38 may include one or more microprocessors, a computer, a portable communication device configured to process data (e.g., a cellular phone, a tablet, laptop computer, etc.) etc. Off-board computer 38 may be connected to controller 34 via network configured to exchange data (e.g., cellular network, LAN, CAN, data bus, Ethernet, Internet, telephone, satellite, etc.).

Controller 34 may be further configured to store and/or receive gearbox data via communication module 36. Gearbox data may be generated off-board the monitoring system (e.g., via sensory or analytical equipment not included in system 28), which may be used by controller 34 to estimate the remaining useful life of gearboxes 22a-c. Gearbox data may include data pertaining to gearboxes 22a-c, internal components of gearboxes 22a-c, and or lubricant of gearboxes 22a-c. For example, gearbox data may include more detailed lubricant parameters that are indicative of the remaining useful life of gearboxes 22a-c, such as types of materials contained within the debris particles (e.g., metals, plastics, organic elements, inorganic elements, etc.). Such gearbox data may be generated in a laboratory or other facility and transmitted to controller 34 via communication module 36, manual entry, or other suitable means of data transfer.

An exemplary process 200 for monitoring one or more of gearboxes 22a-c that may be performed with gearbox monitoring system 28 will be discussed below with regard to FIG. 2.

INDUSTRIAL APPLICABILITY

The disclosed gearbox monitoring system may be used in any machine that employs one or more gearboxes that contain a lubricant, where it is beneficial to estimate a remaining useful life of the gearbox, its components, or the lubricant contained therein. The disclosed gearbox monitoring system finds particular applicability within mobile machines having gearboxes that require periodic replacement and/or lubricant changes caused by wearing and/or failure of internal components. Exemplary operations of gearbox monitoring system 28 will now be described in detail with reference to FIG. 2.

During operation of machine 10, gearboxes 22a-c may begin to wear and their components (e.g., gears, bearings, shafts, etc.) may shed wear particles into the lubricant contained within the respective gearbox. Gearbox monitoring system 28 may constantly monitor the accumulation of wear particles and other debris in gearboxes 22a-c and estimate a remaining useful life of gearboxes 22a-c and their lubricants. While machine 10 is in operation, gearbox monitoring system 28 may estimate the remaining useful life of gearboxes 22a-c according to exemplary process 200 shown in FIG. 2. For the purposes of this disclosure, exemplary process 200 will be described with respect to final drive 22c. It is understood, however, that gearbox monitoring system 28 may be used to monitor each gearbox 22a-c of drive system 16 in a similar manner.

Figure 2:
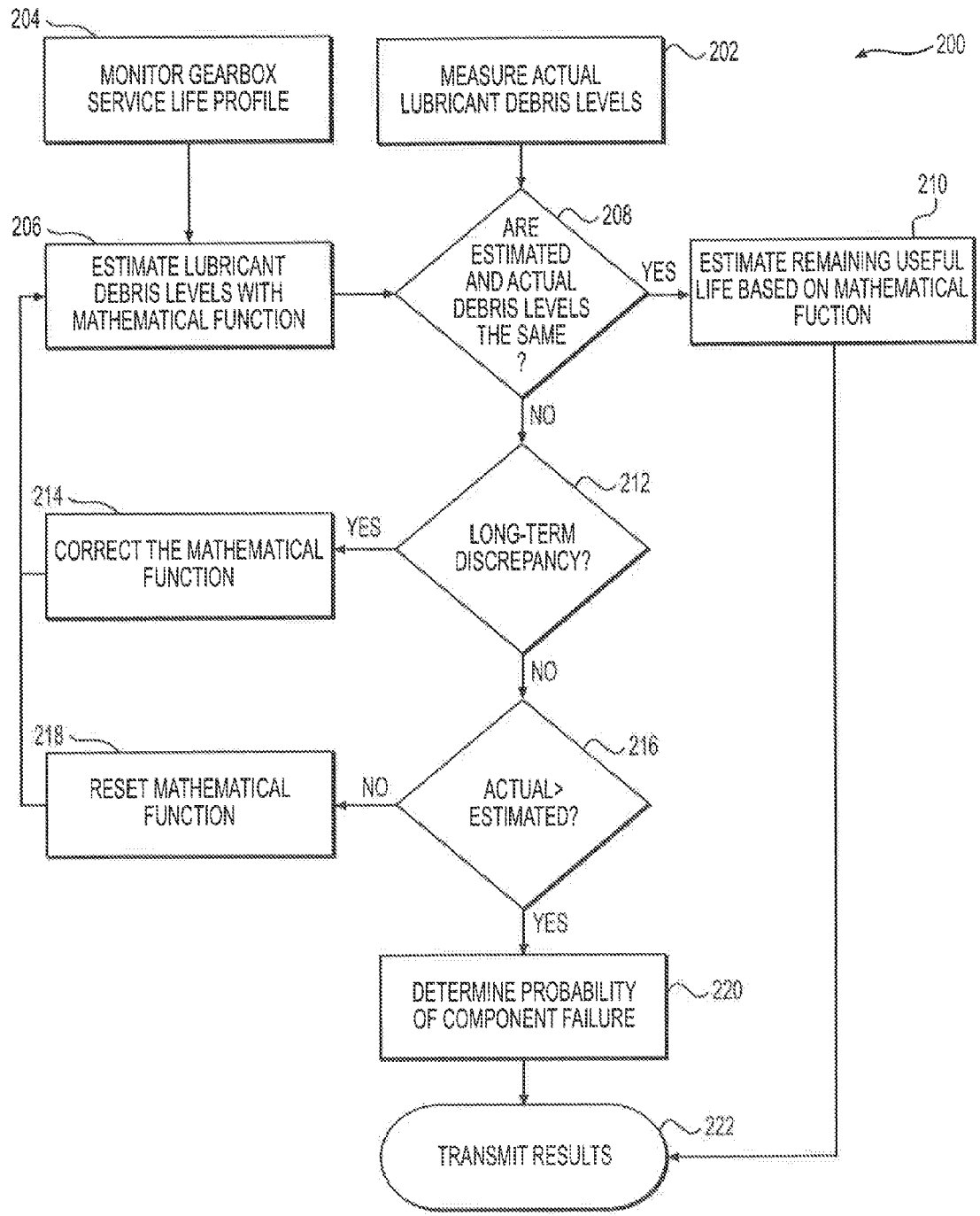
FIG. 2 is a flow chart of an exemplary disclosed process of monitoring a gearbox that may be carried out by the monitoring system of FIG. 1.

As shown in FIG. 2, particle sensor 30 may measure actual concentrations of debris particles in the lubricant of final drive 22c (Step 202) and communicate the concentrations to controller 34 for further processing. Particle sensor 30 may measure the concentration of debris particles at any suitable location within final drive 22c or its lubricant system. For example, particle sensor 30 may measure particle concentrations near the top, middle, or bottom of final drive 22c, in a lubricant sump associated with final drive 22c, or in fluid lines for circulating the lubricant of final drive 22c. Particle sensor 30 may count a number of particles in the lubricant and report the number of counted particles as a concentration of measured particles in a given volume of lubricant (e.g., a number of particles per milliliter of lubricant).

Particle sensor 30 may also determine the size of debris particles counted at step 202. The counted particles may be tabulated by their size, and measured particle concentrations may be reported based on the size or range of sizes of the counted particles. In some embodiments, particle sensor 30 may simultaneously measure concentrations of particles of one or more sizes or size ranges and report the concentrations according to any known convention, such as an ISO reporting convention. For example, particle sensor 30 may measure concentrations for particles 1-100 μm and report the concentrations to controller 34 for further processing. It is understood that concentrations for more or other particle sizes may be measured, reported, and analyzed.

While particle concentrations are being measured by particle sensor 30, gearbox monitoring system 28 may monitor a service life profile of final drive 22c since a previous gearbox replacement or lubricant change (Step 204). The service life profile of final drive 22c may include a number of measurable operating parameters that can be used by controller 34 to estimate a degree of wear of final drive 22c. For example, sensors 32 may generate data indicative of deterioration of final drive 22c, such as an input torque of the final drive 22c, an input speed of final drive, a temperature (e.g., ambient, of final drive 22c, etc.), a lubricant parameter (e.g., temperature, viscosity, pressure, etc.), and/or other data, and report the data to controller 34 for further processing. In some embodiments, gearbox data generated off-board ("off-board data") from monitoring system 28 may be received by controller 34. For example, more detailed lubricant parameters that are indicative of the remaining useful life of gearboxes 22a-c, such as contents of debris particles (e.g., metals, plastics, organic elements, inorganic elements, etc.) and contaminants (e.g., silicon, calcium, water, etc.) may be generated in a laboratory or other facility and transmitted to controller 34 via communication module 36, manual entry, or other suitable means of data transfer. Controller 34 may then estimate a concentration of wear particles in the lubricant due to the wearing of gears, bearings, and other components of final drive 22c based on the data from the sensors 32 and/or off-board data using a mathematical function (Step 206).

The mathematical function used by controller 34 to determine the estimated concentration of debris, or debris levels, in final drive 22c may include models, algorithms, maps, and/or other functions that relate particle debris concentrations of certain sized particles to the service life profile of final drive 22c. The mathematical functions may be derived using empirical testing, such as by measuring particle concentrations under a variety of operating parameters and formulating maps and/or or equations relating the particle concentrations to the operating parameters. The mathematical functions may also or alternatively be generated using modeling methods, finite element methods, and/or other means for estimating current and future particle levels from sensed operating parameters.

Controller 34 may then determine whether the estimated debris level and the actual debris level determined in steps 206 and 202, respectively, are about the same (Step 208). To determine whether the estimated and actual debris levels are about the same, controller 34 may analyze measured debris concentrations at a point in time and/or over a period of time and compare the measured concentrations with estimated concentrations over the same period of time. For example, controller 34 may determine a running average of actual particle concentrations over a period of time and compare them to an average of estimated concentrations over the same time period.

The estimated and actual debris levels may be about the same at step 208 when controller 34 determines that a difference between the actual and estimated particle concentrations is below a first threshold difference $\theta_1$. The difference between the actual and estimated particle concentrations may be an indication that the two values are different, such as a difference by subtraction, a difference by a factor, a difference shown by ratio, a qualitative difference, a difference shown by percentage, etc. The first threshold difference $\theta_1$ may represent an amount (e.g., a concentration amount), a percentage, a factor, a ratio, or a qualitative parameter by which the estimated and actual concentrations are allowed to differ before the estimated concentration is deemed to be an inaccurate estimation of the actual concentration for the purposes of estimating the remaining useful life of final drive 22c and its lubricant.

When the determination at step 208 is "yes," that is, when the difference between the measured concentration and the estimated concentration of debris particles over the specified period of time is below the first threshold difference $\theta_1$, controller 34 may estimate the remaining useful life of final drive 22c using the mathematical function to estimate future particle concentrations (Step 210). In other words, when the determination at step 208 is "yes," the mathematical function may accurately estimate the actual particle concentration within final drive 22c and may be used to accurately forecast future particle concentrations. Controller 34 may then determine future particle concentrations with the mathematical function and use them to estimate the remaining useful life of final drive 22c at step 210.

Controller 34 may store in its memory one or more maps, models, and/or algorithms that correlate estimated particle concentrations to the remaining useful life of final drive 22c for use at step 210. Such maps, models, and algorithms may be generated by empirical testing that indicates the remaining useful life of final drive 22c after various concentrations of wear particles have been measured. The maps, models, and algorithms may also or alternatively be generated using modeling methods, finite element methods, and/or other analytical methods.

The remaining useful life of the gearbox estimated in step 210 may be based on the difference between the measured actual concentrations of debris particles and the service profile-based estimations of particle concentrations over the specified period of time. The remaining useful life may also be based on the off-board data received by controller 34, if desired. The off-board data may be indicative of the deterioration of the gearbox (e.g., deterioration of specific components, levels of specific contaminants, etc.) and used by controller 34 in addition to measured and estimated particle concentrations to estimate the remaining useful life of the gearbox. This combined use of actual particle concentrations and service profile-based estimations of particle concentrations may help ensure the accuracy of the remaining useful life of final drive 22c estimated by gearbox monitoring system 28. After estimating the remaining useful life of final drive 22c at step 210, controller 34 may advance to the end of process 200 and transmit the estimated remaining useful life off-board machine 10 (e.g., to off-board computer 38) via communication module 36 (Step 222).

When the determination at step 208 is "no," that is, when the difference between the measured concentration and the estimated concentration of debris particles over the specified period of time is above the first threshold difference $\theta_1$, controller 34 may then determine whether the difference is a long-term discrepancy (Step 212). A long-term discrepancy may exist when a difference between the estimated and actual particle concentrations is greater than the first threshold difference $\theta_1$ but below a second higher threshold difference $\theta_2$ determined over a relatively long period of time (e.g., more than about 40 hours). A long-term discrepancy may exist due to an inaccuracy of the mathematical function used by controller 34 to estimate particle concentrations in the lubricant of final drive 22c. Such inaccuracies may be caused by variances in operating conditions (e.g., temperature, ground conditions, air conditions, humidity, etc.), load variances (e.g., variances in input torque, input speed, payload, axle load, etc.), manufacturing blemishes or defects present in gearbox components, residual particles left after a previous lubricant change, unexpected failures, etc.

The second threshold difference $\theta_2$ may represent an amount (e.g., a concentration amount), a percentage, a factor, a ratio, or a qualitative parameter by which the estimated and actual concentrations are allowed to differ before it is determinable that a component of final drive 22c (e.g., gear, bearing, shaft, etc.) is likely failing or has likely failed and has caused the increased particle concentration. Generally, gearbox components may shed wear particles at a gradually increasing rate followed by a more sharply increasing rate near the end of their useful life. This behavior may be empirically observed and used to characterize a pattern of wear. However, when gearbox components fail unpredictably (e.g., crack, break, dislodge, become overworn etc.), the actual debris concentration measured by particle sensor 30 may increase by a greater amount than the estimated concentration increases, which may render the estimated particle concentration an inaccurate characterization of the actual particle concentration. Thus, when the measured particle concentration within final drive 22c becomes greater than the estimated particle concentration by at least the second threshold difference $\theta_2$, the probability that a component of final drive 22c is failing or has failed may increase.

When the determination at step 212 is "yes," that is, when the difference between the measured concentration of debris particles and the estimated concentration of debris particles over the specified period of time is above the first threshold difference $\theta_1$ and below the second threshold difference $\theta_2$, controller 34 may then correct the mathematical function used to determine the estimate debris levels based on the difference (Step 214). Controller 34 may correct the mathematical function by adjusting terms within an algorithm or by applying corrective terms to map relationships based on the difference. For example, controller 34 may modify or add a term in an algorithm or map determination to adjust the estimated debris levels by a step amount or an amount with respect to time in order to better reflect the actual debris levels. By correcting the mathematical function for estimating particle concentrations, controller 34 may produce more accurate particle concentration estimations, thereby leading to more accurate estimations of the remaining useful life of final drive 22c.

When the determination at step 212 is "no," indicating that the difference between the estimated and measured particle concentrations is not a long term discrepancy, controller 34 may determine whether the difference is greater than the second threshold difference $\theta_2$, which may indicate that the difference is a short-term discrepancy. A short-term discrepancy may exist when a difference between the estimated and actual particle concentrations is greater than the second threshold difference $\theta_2$ over a relatively short period of time (e.g., less than about 40 hours). Thus, when the determination at step 212 is "no," controller 34 may then determine whether the actual or measured particle concentration is greater than the estimated particle concentration (Step 216).

When the measured concentration of debris particles is less than the estimated concentration of debris particles at step 216 by at least a third threshold difference $\theta_3$ over the specified period of time, the amount of debris particles in the lubricant of final drive 22c may have unexpectedly decreased in a relatively short period of time, and controller 34 may determine that the lubricant or a gearbox component has been replaced. A sudden decrease in the actual particle concentration may occur after the lubricant in final drive has been changed (e.g., the lubricant has been drained and replaced with fresh lubricant) or a gearbox component has been replaced. When the determination at step 216 is "no," that is, when controller 34 determines that the actual particle concentration in the lubricant of final drive 22c has decreased by at least the third threshold difference $\theta_3$ with respect to the estimated particle concentration, controller 34 may "reset" the mathematical function used in step 206 to account for the fresh lubricant or gearbox component (Step 218).

Resetting the mathematical function may include accounting for the size as well as the concentration of debris particles in the lubricant of final drive 22c. Decreased concentrations of certain sized particles may be indicative of whether the lubricant, a gearbox component, or both have been replaced. For example, a decrease in overall particle concentrations may indicate that the lubricant in final drive 22c has been recently replaced. Decreases in concentrations of particular sizes of particles may indicate that a gearbox component has been replaced. For example, reduced accumulation rates of particles of certain sizes after a step decrease in concentration may indicate that gearbox components shedding particles of those sizes may have been replaced.

Resetting the mathematical function may further include resetting time counters used to determine long- and short-term discrepancies at steps 212 and 216, respectively. Further, resetting the mathematical function may include accounting for lubricant parameters (e.g., of fresh lubricant), such as viscosity, weight, additives, and the age of gearbox components (e.g., of fresh components), such as gears, bearings, shafts, etc., and/or other parameters that affect deterioration and wear rates of gearbox components.

When the measured particle concentration is greater than the estimated particle concentration at step 216, the amount of debris particles in the lubricant of final drive 22c may have unexpectedly increased in a relatively short amount of time. A sudden increase in the actual particle concentration may occur when a gearbox component fails unpredictably (e.g., cracks, breaks, dislodges, etc.). Thus, when the measured particle concentration within final drive 22c becomes greater than the estimated particle concentration by at least a fourth threshold difference $\theta_4$, the probability that a component of final drive 22c has failed may be increased.

When the determination at step 216 is "yes," that is, when controller 34 determines that the actual particle concentration in the lubricant of final drive 22c has increased by at least the fourth threshold difference $\theta_4$ with respect to the estimated particle concentration, controller 34 may determine the probability of a gearbox component failure (Step 220). Controller 34 may determine the probability of a gearbox component failure based on the measured particle concentration and particle size data from step 202 and/or the service life profile of final drive 22c monitored at step 204.

For example, the probability that a gearbox component has failed may be increased when controller 34 determines that the concentration of large particles has unexpectedly increased. The presence of large particles in the lubricant of final drive 22c may indicate that a gear or a bearing therein has been cracked, chipped, ground, or dislodged. Increased deterioration of final drive 22c, as determined from the service life profile, may further increase the probability that a gearbox component has failed in such a way. On the other hand, increased concentrations of small particles in the lubricant may indicate that a bearing or gear is over-worn or that the lubricant has been contaminated by a different material (e.g., by dust, dirt, sand, other fluids, etc.).

Controller 34 may determine the probability of a gearbox component failure using one or more maps, models, and/or algorithms stored in its memory that correlate estimated particle concentrations and sizes to the probability of component failure within final drive 22c. Such maps, models, and algorithms may be generated by empirically testing under various service profile parameters the probability that a component of final drive 22c has failed after the difference between measured and estimated particle concentrations of various sizes has been determined. The maps, models, and algorithms may also or alternatively be generated using modeling methods, finite element methods, and/or other analytical methods. After determining the probability of component failure at step 220, controller may then advance to the end of process 200 and transmit the probability of component failure of final drive 22c off-board machine 10 (e.g., to off-board computer 38) via communication module 36 (Step 222)

Gearbox monitoring system 28 may estimate the remaining useful life of final drive 22c with greater accuracy and correct inaccuracies when they exist. In particular, gearbox monitoring system 28 may compare estimated debris particle levels and actual debris particle levels in the lubricant of final drive 22c over a period of time to determine whether a discrepancy exists. When no discrepancy exists, gearbox monitoring system 28 may estimate the remaining useful life of final drive 22c based on a mathematical function used to estimate the debris particle levels. When a discrepancy exists, gearbox monitoring system 28 may correct the mathematical function to produce more accurate subsequent estimations or indicate the probability that an internal component of the gearbox has failed based on the discrepancy.

It will be apparent to those skilled in the art that various modifications and variations can be made to the disclosed gearbox monitoring system. Other embodiments will be apparent to those skilled in the art from consideration of the specification and practice of the disclosed gearbox monitoring system. It is intended that the specification and examples be considered as exemplary only, with a true scope being indicated by the following claims and their equivalents.

What is claimed is:

1. A monitoring system for a gearbox containing a lubricant, the monitoring system comprising:
a first sensor configured to measure a concentration of debris particles in the lubricant;
a second sensor configured to generate data indicative of a deterioration of the gearbox; and
a controller in communication with the first and second sensors, the controller being configured to:
estimate a concentration of debris particles in the lubricant based on the data from the second sensor using a mathematical function;
estimate a remaining useful life of the gearbox based on a difference between the concentration of debris particles measured by the first sensor and the concentration of debris particles estimated to be in the lubricant over a period of time; and
correct the mathematical function when the difference between the concentration of debris particles measured by the first sensor and the concentration of debris particles estimated to be in the lubricant over a period of time is above a first threshold difference and below a second threshold difference.

2. The monitoring system of claim 1, wherein the controller is configured to estimate the remaining useful life of the gearbox using the mathematical function when the difference between the concentration of debris particles measured by the first sensor and the concentration of debris particles estimated to be in the lubricant over a period of time is below a threshold difference.

3. The monitoring system of claim 1, wherein the controller is further configured to determine that the lubricant or a gearbox component has been replaced when the concentration of debris particles measured by the first sensor is less than the concentration of debris particles estimated to be in the lubricant by at least a threshold difference over a period of time.

4. The monitoring system of claim 3, wherein:
the first sensor is further configured to measure a size of debris particles in the lubricant; and the controller is further configured to determine when a gearbox component has been replaced based on the size of the debris particles in the lubricant.

5. The monitoring system of claim 1, wherein the controller is further configured to determine a probability of a gearbox component failure when the concentration of debris particles measured by the first sensor is greater than the concentration of debris particles estimated to be in the lubricant by at least a threshold difference over a period of time.

6. The monitoring system of claim 5, wherein:
the first sensor is further configured to determine a size of debris particles in the lubricant; and
the controller is further configured to determine the probability of a gearbox component failure based on the size of the debris particles in the lubricant.

7. The monitoring system of claim 1, wherein:
the monitoring system further includes a communication module and an off-board computer; and
the controller is connectable to the communication module and further configured to transmit at least one of the data indicative of the deterioration of the gearbox and the remaining useful life of the gearbox to the off-board computer via the communication module.

8. The monitoring system of claim 7, wherein the controller is further configured to receive off-board data indicative of the deterioration of the gearbox and estimate the remaining useful life of the gearbox based on the off-board data.

9. The monitoring system of claim 1, wherein the data indicative of the deterioration of the gearbox includes at least one of a torque of the gearbox, a speed of the gearbox, a temperature, or a lubricant parameter.

10. A method of monitoring a gearbox, comprising:
measuring a concentration of debris particles in a lubricant of the gearbox using a first sensor;
determining a data indicative of a deterioration of the gearbox using a second sensor;
estimating, via a controller, a concentration of debris particles in the lubricant based on the data using a mathematical function stored in a memory of the controller;
estimating a remaining useful life of the gearbox, via the controller, based on a difference between the concentration of debris particles measured and the concentration of debris particles estimated to be in the lubricant; and
correcting the mathematical function, via the controller, when the difference between the concentration of debris particles measured and the concentration debris particles estimated to be in the lubricant over a period of time is above a first threshold difference and below a second threshold difference.

11. The method of claim 10, further comprising determining the remaining useful life of the gearbox using the mathematical function when the difference between the concentration of debris particles measured and the concentration of debris particles estimated to be in the lubricant over a period of time is below a threshold difference.

12. The method of claim 10, further comprising determining that the lubricant or a gearbox component has been replaced when the concentration of debris particles measured is less than the concentration of debris particles estimated to be in the lubricant by more than a threshold difference over a period of time.

13. The method of claim 12, further comprising:
measuring a size of debris particles in the lubricant; and
determining when a gearbox component has been replaced based on the size of the debris particles in the lubricant.

14. The method of claim 10, further comprising determining a probability of a gearbox component failure when the concentration of debris particles measured is greater than the concentration of debris particles estimated to be in the lubricant by more than a threshold difference over a period of time.

15. The method of claim 14, further comprising:
determining a size of debris particles in the lubricant; and
determining the probability of a gearbox component failure based on the size of the debris particles in the lubricant.

16. The method of claim 10, further including determining the data indicative of the deterioration of the gearbox includes determining at least one of a torque of the gearbox, a speed of the gearbox, a temperature, and or a lubricant parameter.

17. The method of claim 10, wherein:
the gearbox forms a portion of a drive system for a mobile machine; and
the method further includes transmitting at least one of the data indicative of the deterioration of the gearbox and the remaining useful life of the gearbox off-board the machine.

18. A mobile machine, comprising:
a frame;
a power source mounted to the frame;
a traction device mounted to the frame;
a gearbox drivingly connected between the power source and the traction device, wherein the gearbox contains a lubricant;
a first sensor configured to measure a concentration of debris particles in the lubricant;
a second sensor configured to generate data indicative of a deterioration of the gearbox; and
a controller in communication with the first and second sensors, the controller being configured to:
estimate a concentration of debris particles in the lubricant based on the data from the second sensor using a mathematical function;
estimate a remaining useful life of the gearbox using the mathematical function when a difference between the concentration of the debris particles measured by the first sensor and the concentration of debris particles estimated to be in the lubricant over a period of time is below a first threshold difference; and
correct the mathematical function when the difference between the concentration of debris particles measured by the first sensor and the concentration of debris particles estimated to be in the lubricant over the period of time is above the first threshold difference and below a second threshold difference.

* * * * *